United States Patent [19]

Edwards et al.

[11] Patent Number: 5,398,683
[45] Date of Patent: Mar. 21, 1995

[54] COMBINATION MONOPHASIC ACTION POTENTIAL/ABLATION CATHETER AND HIGH-PERFORMANCE FILTER SYSTEM

[75] Inventors: Stuart D. Edwards, San Ramon, Calif.; Michael R. Franz, Washington, D.C.; Russel B. Thompson, San Leandro; Roger A. Stern, Cupertino, both of Calif.

[73] Assignee: EP Technologies, Inc., Sunnyvale, Calif.

[21] Appl. No.: 92,762

[22] Filed: Jul. 16, 1993

Related U.S. Application Data

[63] Continuation of Ser. No. 705,627, May 24, 1991, abandoned.

[51] Int. Cl.⁶ ............................................. A61B 5/04
[52] U.S. Cl. ............................ 128/642; 607/116; 607/122; 607/154
[58] Field of Search .............. 128/642; 607/116, 122, 607/154, 155; 606/41, 34

[56] References Cited

U.S. PATENT DOCUMENTS

| | | | |
|---|---|---|---|
| 4,641,649 | 2/1987 | Walinsky et al. | 128/784 X |
| 4,785,815 | 11/1988 | Cohen | 128/642 |
| 4,832,048 | 5/1989 | Cohen | 606/41 |
| 4,892,102 | 1/1990 | Astrinsky | 128/642 |
| 4,922,912 | 5/1990 | Watanabe | 128/642 |
| 4,945,912 | 8/1990 | Langberg | 128/786 X |
| 4,955,382 | 9/1990 | Franz et al. | 128/786 X |
| 5,156,151 | 10/1992 | Imran | 128/642 |
| 5,230,349 | 7/1993 | Langberg | 607/122 |

*Primary Examiner*—Kyle L. Howell
*Assistant Examiner*—Brian L. Casler
*Attorney, Agent, or Firm*—Ryan, Kees & Hohenfeldt

[57] ABSTRACT

A combination catheter for both detecting monophasic action potentials and ablating surface tissue in an in vivo heart of a patient is provided. The apparatus includes a catheter probe having a terminal tip portion and an electrode carried on the tip such that a portion of the tip electrode is exposed to ambient. A reference electrode is spaced along the tip from the first electrode for supplying a reference potential signal. An ablating electrode is located adjacent to but electrically insulated from both the tip and reference electrodes for providing electromagnetic energy to the tip. The electrodes are electrically connected to the proximal end of the catheter through individual conductors or wires that run through an insulated cable. An electronic filter is provided to permit the recording of MAPs during ablation without radiofrequency interference. The catheter may also include standard mapping and/or pacing electrodes. The catheter may further include a steering mechanism for positioning the catheter at various treatment sites in the heart, and a structure for holding the tip electrode in substantially perpendicular contact with heart tissue with a positive pressure, and for spacing the reference electrode from the heart tissue.

8 Claims, 3 Drawing Sheets

COMBINATION MONOPHASIC ACTION POTENTIAL/ABLATION CATHETER AND HIGH-PERFORMANCE FILTER SYSTEM

This is a continuation of application Ser. No. 07/705,627, filed on May 24, 1991, now abandoned.

BACKGROUND OF THE INVENTION

This invention relates to a catheter for the simultaneous or near-simultaneous recording of monophasic action potentials (MAPs) and ablating arrhythmia-causing tissue by coupling radiofrequency energy to tissue surrounding the catheter tip, and more particularly to a method and apparatus for simultaneously recording MAPs and ablating by contacting heart tissue with a small dual MAP/ablating electrode under positive pressure.

The electrical charge of the outer membrane of an individual heart muscle cell is known as the "membrane potential". During each heart beat, the membrane potential discharges (depolarizes) and then slowly recharges (repolarizes). The waveform of this periodic depolarization and repolarization is called the "transmembrane action potential." Mechanistically, the action potential is produced by a well-organized array of ionic currents across the cell membrane.

At the turn of the century, it had already been recognized that a potential similar in shape to the later-discovered transmembrane potential could be recorded if one brought into contact a first electrode with an injured spot of the heart and a second reference electrode with an intact spot. Those signals became known as "injury potentials" or "monophasic action potentials" (MAPs) because of the waveform shape.

The further development of the science of MAPs may be found in U.S. Pat. No. 4,955,382, the disclosure of which is hereby incorporated by reference. It has been recognized that local heart muscle injury is not a prerequisite for the generation of MAPs, and that application of slight pressure with the tip against the inner wall of the heart will result in the generation of monophasic action potential signals. These signals can be recorded reliably (i.e., without distortion) by using direct current (DC) coupled amplification.

One problem to overcome in MAP recordation is the slow DC drift caused by electrode polarization in conventional electrical material used in the recording of intracardiac electrical signals, such as silver or platinum. These materials are polarizable and cause offset and drift-which is not a problem in conventional intracardiac recordings, because those signals are AC coupled, which eliminates offset and drift. The MAPs, however, are to be recorded in DC fashion, and therefore are susceptible to electrode polarization. The use of a silver-silver chloride electrode material yields surprisingly good results in terms of both long-term stability of the signal and extremely low noise levels.

Another important discovery has been that the tip electrode of the catheter should be held against the inner surface of the heart with slight and relatively constant pressure. In order to accomplish this in a vigorously beating heart, a spring-steel stylet is inserted into a lumen of the catheter to act as an elastic spring, keeping the tip electrode in stable contact pressure with the endocardium throughout the cardiac cycle. This leads to major improvements in signal stability.

Another design objective for a good MAP catheter is to ensure a relatively perpendicular position of the electrode tip with the endocardial wall. Again, the spring electrode is useful in this respect. Conventional catheters are usually brought into contact with the heart wall in a substantially tangential manner. Such conventional catheters are designed simply to record intercardiac electrograms, not MAPs. For the monophasic action potential catheter, direct contact between the tip electrode and the endocardium is made. This also keeps the reference electrode, which is located along the catheter shaft, away from the heart muscle.

To facilitate the maneuverability of the catheter during a procedure in the human heart, the distal end of the catheter should be relatively flexible during the time of insertion, and the spring-loading feature preferably comes into action only after a stable position of the catheter tip has been obtained. Thus, in a preferred embodiment the catheter is constructed in such a way that the spring wire situated in the lumen of the catheter is retractable. During catheter insertion, the spring wire or stylet is withdrawn from its distal position by approximately 5 cm, making the tip relatively soft. Once the catheter is positioned, the spring wire is again advanced all the way into the catheter in order to stiffen it and to give it the elastic properties that are important for the described properties. Improved stylets and wires that position the tip electrode perpendicularly to the heart surface with the proper amount of constant pressure are described in U.S. Pat. No. 4,955,382.

Thus, a main feature of a good catheter is the ability to bring into close and steady contact with the inner surface of the myocardial wall a nonpolarizable electrode which both produces and records MAPs. To achieve this property, the electrodes are formed from nonpolarizable material such as silver-silver chloride, and the tip electrode should be maintained at a relatively constant pressure against the myocardial wall, preferably with some type of spring loading.

The catheter of the present invention preferably contains a spring-steel guide wire which provides a high degree of elasticity or resilience, allowing the catheter tip to follow the myocardial wall throughout the heartbeat without losing its contacting force and without being dislodged. The inner surface of the heart is lined with crevices and ridges (called the trabeculae carneae) that are helpful in keeping the spring-loaded catheter tip in its desired location. The contact pressure exerted by the tip electrode against the endocardial wall is strong enough to produce the amount of local myocardial depolarization required to produce the MAP. The contact pressure is, on the other hand, soft and gentle enough to avoid damaging the endocardium or the myocardium or cause other complications. In particular, no cardiac arrhythmias are observed during the application of the catheter. Usually a single extra beat is observed during the initial contact of the catheter tip against the wall.

The tip electrode is responsible for the generation and the recording of the MAP itself. A reference electrode, or "indifferent" electrode, required to close the electrical circuit, is located approximately 3 to 5 mm from the tip electrode in the catheter shaft and is embedded in the wall so that it is flush with or slightly recessed in the catheter shaft. In this position, the electrode makes contact only with the surrounding blood and not with the heart wall itself.

This reference electrode is brought into close proximity with the tip electrode, since the heart as a whole is a forceful electrical potential generator and these potentials are everywhere in the cardiac cavities. If the reference electrode were in a remote location, then the amplifier circuit would pick up the QRS complex.

Another feature of this invention relates to thermal destruction, or ablation. Ablation of abnormal myocardial tissue (such as arrhythmia-causing tissue) is a therapeutic procedure used with increasing frequency for treatment of cardiac arrhythmias such as, for example, ventricular tachycardia. The medical technique of ablation is discussed in G. Fontaine et al., *Ablation in Cardiac Arrhythmias* (New York: Futura Publishing Co., 1987), and D Newman et al., "Catheter Ablation of Cardiac Arrhythmias", in *Current Problems in Cardiology*, Year Book Medical Publishers, 1989.

Catheter ablation of ventricular tachycardia was first described in 1983 as a method for destroying arrhythmia-causing tissue. Typically, a pacing catheter is introduced into the left ventricle of the heart, and manipulated until the site of earliest activation during ventricular tachycardia is found, indicating the location of the problem tissue. Electrical energy, often high voltage DC pulses are then applied between a catheter-mounted electrode and an external chest wall electrode. In this way, arrhythmia-causing cardiac tissue is destroyed.

More recently, less drastic methods than high voltage pulses have been developed, which are painful (requiring general anaesthesia), and dangerous due to arcing and explosive gas formation at the catheter tip. The use of electromagnetic energy, more particularly radiofrequency (RF) or microwave energy, is currently in popular use. RF and microwave energy, unless otherwise noted, refers to energy in the electromagnetic spectrum from about 10 kHz to 100 GHz. RF ablation, usually in the range of 300–1200 kHz, is a safer alternative to high voltage DC pulsing in which RF energy is applied to the endocardium via an catheter electrode. Tissue destruction, or ablative injury, is effected by heating generated by the RF electric field. RF ablation results in a more controllable lesion size, with no gas or shock wave formation. Ablation may also be effected with energy having microwave frequencies, from about 700 MHz to 100 GHz.

Currently, no reliable on-line method exists to quickly and accurately determine whether radiofrequency (RF) energy application has resulted in lesions of a size sufficient to destroy the injured myocardial tissue. That is primarily because previously, no provision has been made for accurately measuring the electrophysiological activity of the heart in the immediate vicinity of heart tissue which is being ablated by an ablating catheter. Moreover, if it is desired to pace the heart at the same time as measuring MAPs in the heart, two entrance sites to the patient must be created and two catheters must be utilized, which is highly undesirable.

Because of the complexity of electrical cardiac activity, when a pacing or ablating electrode is inserted into the heart, and it is desired to measure the resulting monophasic action potentials of the heart, it would be of extreme usefulness to be able to measure such potentials in the vicinity of the ablation, rather than at a more remote location.

Important applications of the present invention are in the areas of studying and treating myocardial ischemia and cardiac arrhythmias. In particular, the present invention permits (1) precisely locating areas of myocardial ischemia by studying localized MAPs and directly treating them; and (2) diagnosing the nature and locality of arrhythmias originating from after-depolarizations and treating those arrhythmias. These after-depolarizations have heretofore been detected only in isolated animal tissue preparations where microelectrodes can be applied. The MAP/ablation catheter is a tool that can allow the clinical investigator to detect and remedy such abnormal potentials in the human heart and thereby significantly broaden the ability to diagnose this group of arrhythmias.

SUMMARY OF THE INVENTION

The present invention overcomes the drawbacks in the prior art by permitting ablation both in the same region where MAPs are being recorded, and at the same or nearly the same time as they are being recorded. The system uses an electronic filter system to eliminate radiofrequency interference that would otherwise prevent simultaneous ablation and recordation. Although simultaneous ablation and EKG reading has previously been possible, simultaneous ablation and MAP recordation offers more information to the user, as the MAP signal is a more sensitive indicator of tissue viability.

Previously, simultaneous ablation and MAP recording was possible using two catheters. However, this method was more invasive and more uncertain, as situating the two catheters at precisely the same location was difficult or impossible. Therefore, the present invention provides a heretofore unavailable single ablating catheter capable of being a precise instantaneous indicator of thrombus conditions or tissue death.

By permitting ablation and MAP recordation at approximately the same time and same location in the heart, the present invention also potentially minimizes the necessary lesion size, as ablation may be stopped immediately upon recognition of tissue death.

Therefore, it is an object of the present invention to provide an apparatus for measuring monophasic action potentials and, at about the same time, ablating surface myocardial tissue with electromagnetic energy.

It is another object of the present invention to provide an apparatus for measuring monophasic action potentials and, at about the same time, ablating surface myocardial tissue with radiofrequency energy.

A further object of the present invention is to provide a MAP measuring apparatus which can accurately record action potentials and ablate surface myocardial tissue over sustained periods of time.

Another object of the present invention is to provide a MAP measuring apparatus which can ablate surface myocardial tissue and measure action potentials in a vigorously beating in-situ heart.

Another object of the present invention is to provide a method of using the apparatus for recording MAPs while simultaneously ablating surface myocardial tissue, or immediately before or after ablating surface myocardial tissue.

A further object of the present invention is to provide a method of detecting and correcting ischemia by sensing MAPs and, at approximately the same time and location in the heart, ablating surface myocardial tissue.

In accordance with the above objects, the present invention includes an apparatus for both detecting monophasic action potentials and ablating surface tissue in an in vivo heart of a patient. The apparatus comprises a catheter probe having a terminal tip portion and a first electrode carried on the tip such that a portion of the first electrode is exposed to ambient. A second electrode is spaced along the tip from the first electrode for supplying a reference potential signal. A third electrode is located adjacent to the first electrode but electrically insulated from both the first and second electrodes for providing electromagnetic energy, preferably radiofrequency or microwave energy.

The electrodes are electrically connected to the proximal end of the catheter through individual conductors or wires that run through an insulated cable. In one embodiment of the invention, coaxial cable may be used as the conductors and cable together. The connection of one conductor to the third electrode (the ablation electrode) will include an antenna for receiving electromagnetic energy. The antenna may be formed by the conductor itself, or may be a separate component, such as a conductor wound in the form of a helix. Helical antennas, and their connection in an ablating catheter system, are described in U.S. Pat. No. 4,945,912, the disclosure of which is hereby incorporated by reference.

The system of this invention may also include a steering mechanism for positioning the catheter in various locations in the heart. The mechanism permits the distal end of the catheter to be bent into varying shapes, and will include proximally located controls, a flexible steering shaft, and a distal apparatus for bending the distal end. Suitable steering mechanisms are disclosed in commonly-owned, copending U.S. application Ser. No. 07/473,667, the disclosure of which is hereby incorporated by reference.

In accordance with further aspects of the invention, an electronic filter is provided to permit the recording of MAPs during ablation without radiofrequency interference. The probe may also be provided with a structure for holding the first electrode in contact with heart tissue with a positive pressure without causing significant macroscopic damage to the heart tissue and for orienting the probe such that the second electrode is spaced from the heart tissue and the third electrode remains near the heart tissue.

The first and second electrodes of this invention are non-polarizable, preferably formed of silver-silver chloride, to avoid direct current drift during the course of investigation.

BRIEF DESCRIPTION OF THE DRAWINGS

FIG. 7 is an electrical schematic of the electronic filter system of the invention.

DETAILED DESCRIPTION OF THE INVENTION

Figure 1:
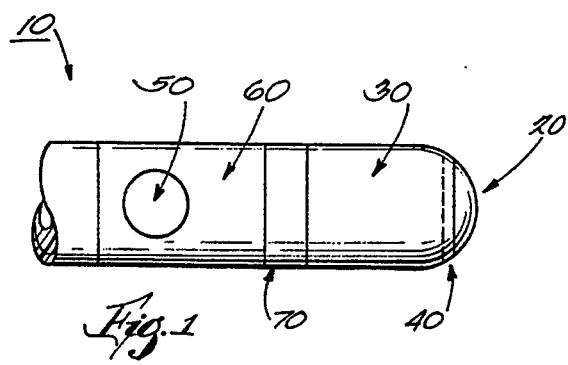
FIG. 1 is a schematic view of the tip portion of the apparatus of the invention.
Figure 2:
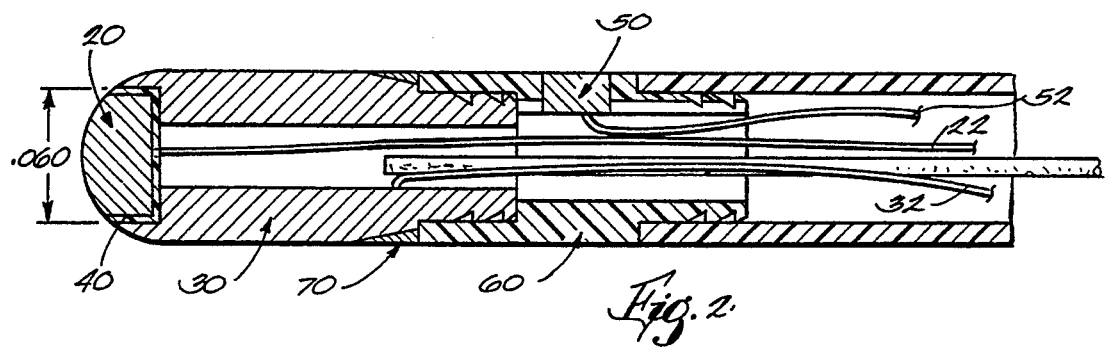
FIG. 2 is a sectional view of the tip portion shown in FIG. 1.

FIGS. 1 and 2 show the tip portion 10 of a probe according to the present invention. Tip 10 comprises an exposed tip electrode 20 for detecting monophasic action potentials. Electrode 20 is a sintered depolarizing electrode, preferably formed of silver-silver chloride. Adjacent to, but electrically insulated from the tip electrode is the ablating electrode 30. Electrode 30 is preferably formed of stainless steel or platinum, and is insulated from electrode 20 by skirt 40. Skirt 40 may be made of Teflon tubing, for example, or any other insulating material. Skirt 40 has a thickness of 0.001–0.200 inches, most preferably 0.002–0.020 inches.

In this manner, the ablating electrode 30 is located in close proximity to the MAP recording tip electrode 20, and the catheter tip will effectively be recording MAP signals at the same location where ablation is taking place. The two electrodes may be as close as possible, limited only by the finite thickness of insulating skirt 40. If the two electrodes are separated by much more than 0.200 inches, however, the ablating electrode may no longer be effectively ablating the area where the MAP signals are recorded, or it may be ablating a different area.

Located proximally from electrode 30 is a side electrode 50, which serves as the "indifferent" electrode for tip electrode 20. Side electrode 50 is electrically insulated from the tip and ablation electrodes by an insulating insert 60. Insert 60 is preferably formed from an insulating material such as plastics or rubbers, more preferably Delrin.

The tip and side electrodes 20 and 50 are preferably formed from a sintered silver-silver chloride material. An alternative structure for the electrodes 20 and 50 is provided by utilizing silver-silver chloride flakes bound together by cyanoacrylate adhesive. It has been found that it is desirable to place side electrode 50 proximally from the tip electrode 20 by a suitable distance as, for example, 3–10 mm, preferably 3–5 mm.

As seen in FIG. 2, electrodes 20, 30 and 50 are electrically connected to the proximal end of the catheter via electrical conductors 22, 32 and 52, respectively. The electrical conductors are formed of a suitable material such as insulated copper and serve as signal wires. Tip electrode 20 is soldered to center conductor 22, which is covered with a teflon sleeve for electrical insulation. Electrical conductor 22 may also act as an antenna for receiving transmitted electromagnetic energy.

FIGS. 1 and 2 also show an ablating skirt 70, which is in fact an optional component of the present invention. Skirt 70 forms a ring on the probe surface at the proximal end of electrode 30. The thickness of skirt 70 varies based on its axial distance from the junction of electrode 30 and insert 60. The thickness of skirt 70 tapers to zero at the distal rim and monotonically increases to about 0.010–0.040 inches at the proximal rim. The skirt is formed from a partially conductive material, preferably a partially conductive epoxy such as a silver epoxy. Proximally located to skirt 70 on the probe surface is insert 60, although electrode 30 may have a tapered base, thereby extending proximally beyond skirt 70 in the probe interior as seen in FIG. 2.

Skirt 70 is formed so that the electrical properties at the electrode-insert junction are tempered. Without the skirt, the junction forms a hot spot and an undesirable charring focus. The presence of a partially conductive skirt with resistive or capacitive properties changes the surface impedance, equalizes the external electric fields and improves radial penetration of the field. By vastly reducing or eliminating the aberrational electrical fields, the skirt eliminates the charring problem.

Figure 3:
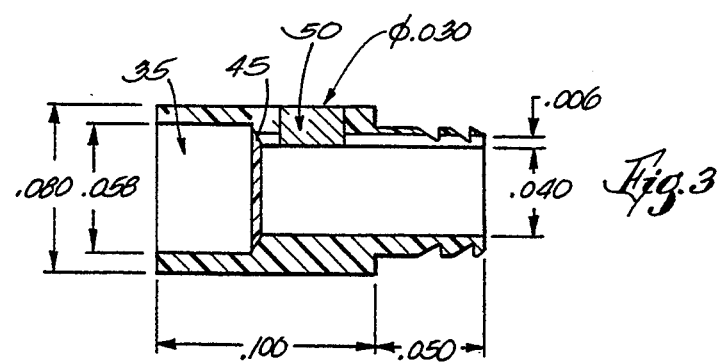
FIG. 3 is another sectional view of an alternate embodiment of the tip portion of the apparatus of the invention.
Figure 6:
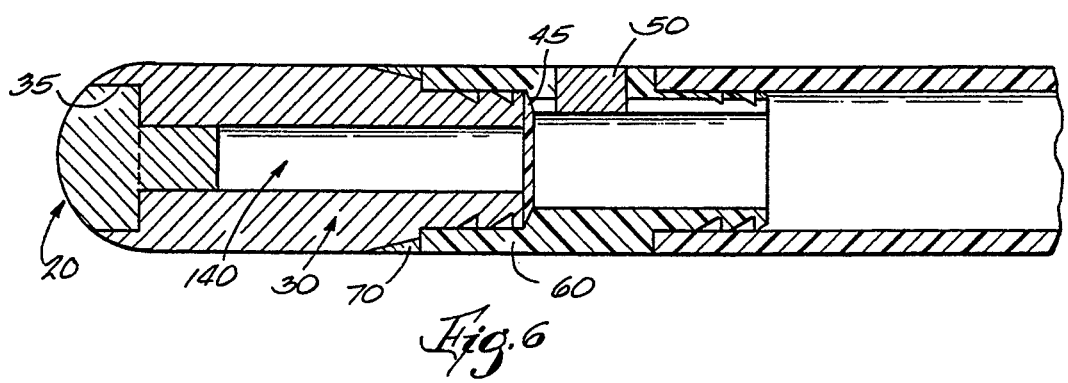
FIG. 6 is another sectional view of an alternate embodiment of the tip portion of the apparatus of the invention.

FIG. 3 shows an alternate embodiment of the housing for the tip and ablating electrodes. Socket 35 is designed to receive electrode 30 (as shown in FIG. 6), which tapers at its base to about 0.058 inches in diameter. When inserted, electrode 30 is thereby fitted in teflon skirt 45 with an inner diameter of about 0.058 inches and an outer diameter of 0.080 inches. Electrode 30 extends about 0.046 inches down the probe and sits on the thin bottom of the teflon skirt.

Figure 4:
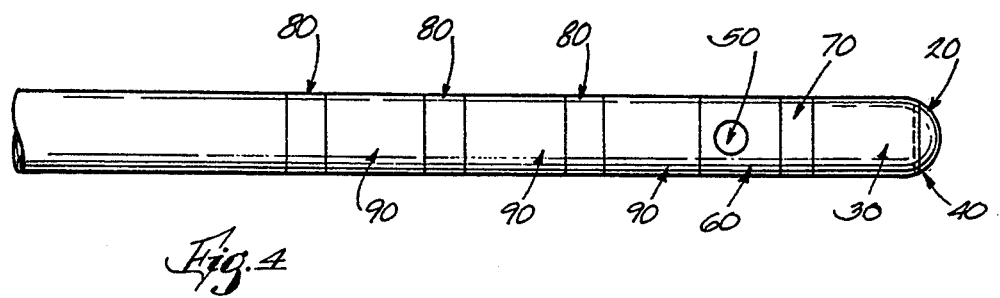
FIG. 4 is a schematic view of the tip portion of an alternate embodiment of the invention.

FIG. 4 shows an alternate embodiment of the catheter of the invention which, in addition to performing simultaneous MAP recordation and radiofrequency ablation, is able to simultaneously perform standard mapping through a number of standard mapping electrodes. The process of mapping through mapping electrodes is well known as described in Zipes et al., *Cardiac Electrophysiology* (Saunders Pub. Co.). The probe shown in FIG. 4 consists of a distal end identical to that shown in FIG. 1, but utilizes a series of proximally located standard mapping electrodes 80 separated by a series of insulating inserts 90. Although the drawing depicts three mapping electrodes, as few as 1 and as many as 16 or more could actually be used.

Figure 5:
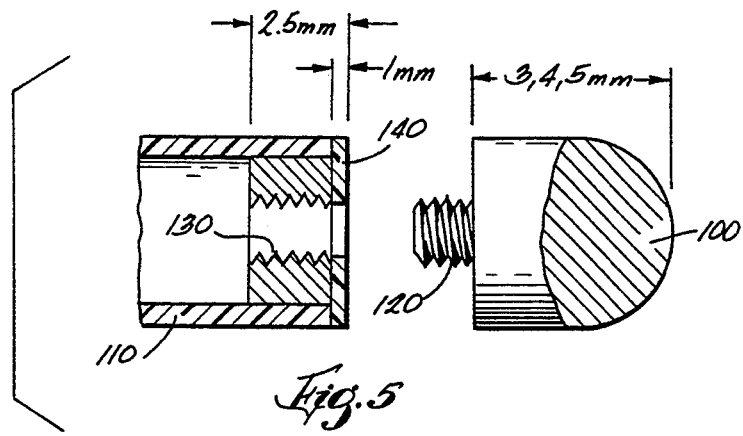
FIG. 5 is a sectional view of a variable tip assembly, an alternate embodiment of the invention.

FIG. 5 shows an alternate embodiment of the tip of the current invention. In this embodiment, a variable tip assembly is utilized so that alternate tip shape or configuration may be easily substituted. Tip shapes including "peanut", "hourglass" or bulbous geometries are contemplated. The tip electrode and ablating electrode are contained on removable head 100, which varies in size from 3–10 mm and attaches to probe 110 through threaded plug 120. Plug 120 is a watchmaker's thread screw and screws into threaded hole 130 to sit on teflon skirt 140. Electrical conductors to the electrodes extend through plug 120 and attach to conductors located centrally in probe 110 through hole 130. Loctite is used to fix head 100 in proper position.

The variable tip assembly configuration of FIG. 5 can be used to provide nonsterilized tips, which can be easily sterilized by conventional methods prior to use, permitting ease of manufacture and use.

FIG. 6 shows yet another alternative embodiment of the catheter of the current invention in which the tip and ablating electrodes have been inserted into socket 35 of the device of FIG. 3. In particular, this figure shows a central bore 140 running from the proximal end of the probe to the tip electrode at the distal tip. Bore 140 contains the electrical conductors that electrically connect the distal electrodes to the proximal end, and may also contain steering wires for controlling catheter steering.

FIG. 7 is a schematic diagram of the electronic filter system of the invention. The filter is a DC-accurate 5 kHz low pass filter that receives the MAP signal from electrode 20 via conductor 22 as shown in FIG. 1. The filter permits passage of frequencies only below 5 kHz. Accordingly, all ablating frequencies (RF and microwave) do not pass, and only MAP signals will pass. The outputs 202 and 203 pass the filtered signal to a display device such as an oscilloscope or strip chart recorder.

The filter in FIG. 7 uses two inputs 200 and 201. These two inputs may be connected to either the distal tip electrode 20, proximal side electrode 50, as shown in FIG. 1, or directly to the skin of the patient. When the inputs are connected to the two electrodes, the system is called a "distal bipolar" system. A distal or proximal "unipolar" system occurs when input 200 is connected to one electrode and input 201 is connected to the patient's skin.

Figure 8:
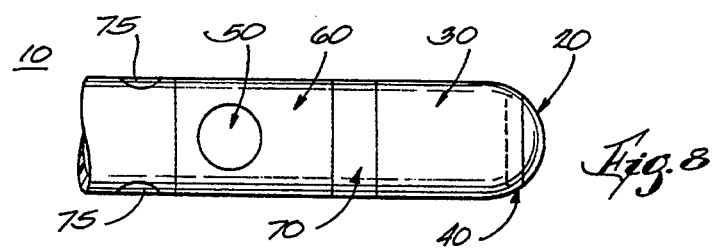
FIG. 8 is a schematic view of a combination MAP/ablation/pacing catheter tip of the invention.

FIG. 8 shows an alternative embodiment of the invention, depicting a catheter 10 which is a combination pacing, ablation and MAP catheter. FIG. 8 is similar to FIG. 1, the difference lying in the presence of a pair of pacing electrodes 75. The function and method of use of pacing electrodes such as electrodes 75 for activating is well known in the art in standard configurations of pacing electrode catheters; that is, the same types of electrical signals which are provided to pacing electrodes in standard pacing catheters may also be provided to the electrodes 75 in the present invention.

The two pacing electrodes 75 are 0.035" platinum dot electrodes, and are positioned substantially diametrically opposite each other on the exterior surface of the catheter. Side electrode 50 is radially positioned halfway between said two pacing electrodes, but may be located axially toward or away from the catheter tip.

Figure 9:
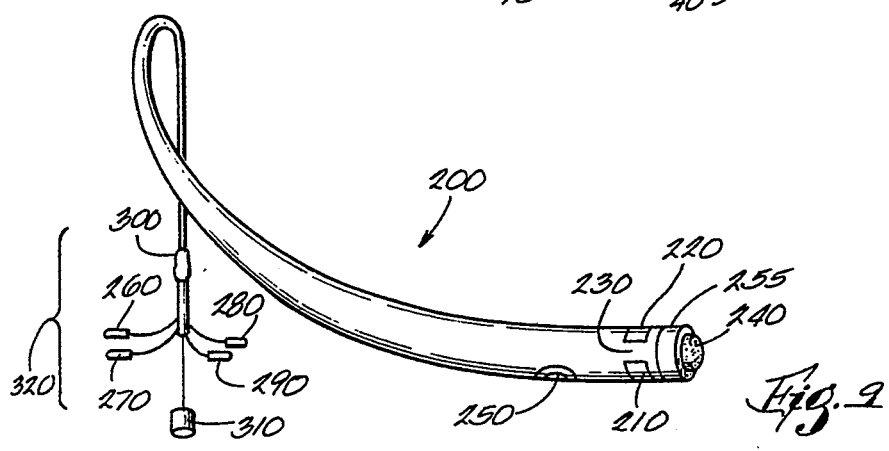
FIG. 9 is an overall schematic view of the catheter system of the invention.
Figure 2:
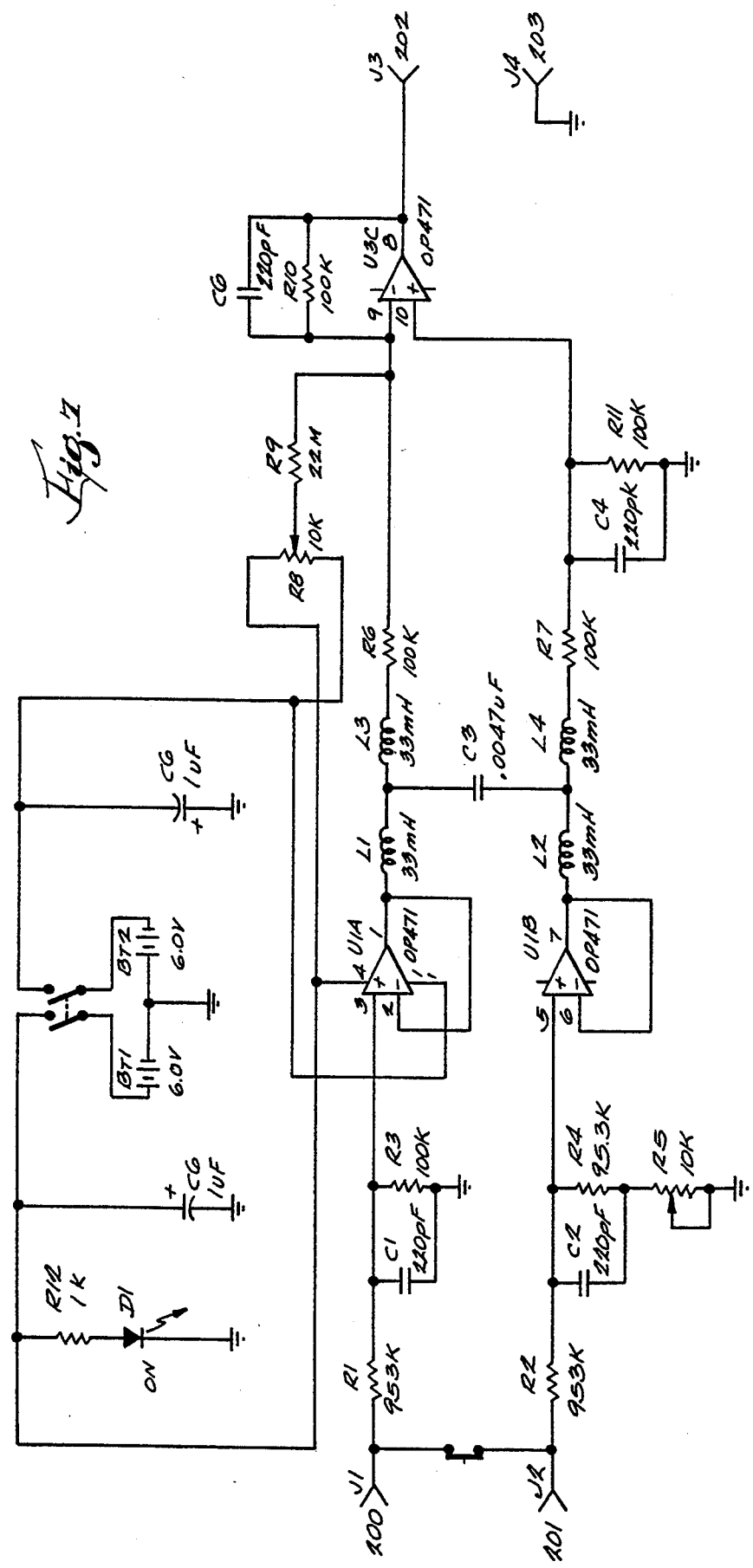

FIG. 9 is a schematic overview of a combination MAP, ablation, and pacing catheter 200, in which pacing electrodes 210 and 220 are mounted at the distal end 230 of the catheter 200. In addition, a tip electrode 240 a side electrode 250, and an ablation electrode 255 are provided, as in the configuration of FIG. 1, and are electrically connected to connections such as plugs 260 and 270.

The pacing electrodes 210 and 220 are similarly connected to plugs 280 and 290, respectively. Plugs 280 and 290 are standard plugs. It will be understood that contained within FIG. 9 are the necessary electrical leads to the electrodes 210, 220, 240, 250 and 255, and in addition stylets and other features as described herein with respect to other embodiments may be included. The electrical lead to electrode 255 may be connected to an electromagnetic energy source, such as a radiofrequency source or microwave source, for providing ablating energy to the catheter tip. The electrical leads to electrodes 240 and 250 may provide input to the RF filter of FIG. 7, as described above.

A coupling 300 for the plugs 260-290 is provided, insuring a reliable connection between the plugs to the electrical leads contained within the catheter 200. This coupling 300 is preferably of a hard material such as polycarbonate, and has an enlarged diameter relative to the catheter 200. This provides greater torque control for the user of the catheter when manipulating the catheter into the heart and positioning the tip electrode 240 against the endocardium.

In addition to the coupling 300, a knurled knob 310 may be attached at the proximal end 320 of the catheter 200. The knob 310 is preferably connected to the catheter 200 in a nonrotatable fashion, such that axial rotation of the knob 310 causes similar axial rotation of the catheter 200. As shown in FIG. 8, the knob 310 may be generally cylindrical in configuration, or may be of some other convenient shape for twisting by hand.

METHODS OF USE

The general principle of identifying ischemic, infarction, and arrhythmia-causing sites using MAPs is described fully in U.S. Pat. No. 4,955,382. That procedure is basically followed in the current invention with the following additions.

To localize and treat myocardial ischemia or ventricular tachycardia, the catheter of the present invention is inserted endocardially, and as the catheter is consecutively placed at multiple endocardial locations, MAP signals are detected until an abnormal condition is discovered. This abnormal condition may be the late arrival of the action potential, or the wrong potential. When the abnormal MAP is detected, RF energy is passed to the ablation electrode to ablate the abnormal tissue. While the ablating RF energy is being dissipated to the tissue, the MAP signal is simultaneously being read and recorded. When the MAP signal has disappeared for a certain period of time, the tissue is presumed dead and ablation may cease.

After the procedure has been performed, the success of the procedure may be determined by conventional methods. For example, the heart may be paced to induce the arrhythmia or tachycardia using pacing electrodes both before and after the procedure.

The ability to simultaneously record MAPs and ablate cardiac tissue with a combination MAP/ablation catheter has been examined in dogs. In one study on 22 left ventricular sites in six closed-chest dogs, RF ablation at 25 watts was applied for 60 seconds or until a rise in impedance occurred. Simultaneous MAP recording throughout each RF application took place using the lowpass filter system described above. Before RF ablation, stable MAP signals of $22\pm7$ mV amplitude were obtained at each site. In 13 RF applications, MAP signal amplitude decreased to less than 20% of baseline within only 3–5 sec of RF ablation. In these cases, power was shut off at 6–8 sec (group A). In 5 RF applications, MAP amplitude decreased more slowly, falling below 20% within 40–60 seconds. In these cases, power was shut off at 60 sec (group B). In the 4 remaining applications, MAP amplitude decreased by only 35–65%, and upon cessation of RF ablation (at 60 sec) recovered to 60–85% of baseline (group C). Post-mortem analysis showed similar lesion volumes in group A and B ($135\pm24$ mm$^3$ vs $88\pm36$ mm$^3$, NS) but smaller lesion volumes in group C ($52\pm32$ mm$^3$; $p<0.05$ vs. group A).

In another set of experiments, application of RF energy of low power and short duration were delivered to the canine heart through the combination MAP/ablation catheter of the current invention to observe the relationship between RF power and duration on one hand and lesions size and change in MAP signal morphology on the other hand. MAP signals were recorded using the low-pass filter and distal bipolar signals, proximal unipolar signals, and distal unipolar signals were all recorded before, during and after RF ablations.

In total four lesions were made in the left ventricle and two in the right ventricle. RF power varied from 5–10 watts and duration varied from 10–60 seconds or until an impedance rise occurred. Changes in MAP signal morphology during and after RF ablation were recorded. These morphology changes can later be correlated to lesion depth, volume and location. The animal is then sacrificed to determine lesion depth, volume and location.

These experiments demonstrate that simultaneous MAP monitoring during RF ablation provides instantaneous feedback about the magnitude and permanence of myocardial tissue destruction, even during very brief RF pulses.

We claim:

1. Apparatus for both detecting monophasic action potentials and ablating surface tissue in an in vivo heart of a patient, comprising:
   a catheter having a proximal end and a distal end, said distal end having a terminal tip and an exterior surface, and said catheter being adapted for insertion into a patient for detecting said monophasic action potentials;
   a first electrode carried at said distal terminal tip for contacting surface tissue of the heart of the patient for measuring potentials at said surface tissue;
   a second electrode carried on said catheter and spaced from said first electrode for supplying a reference potential signal;
   a third electrode carried on said catheter adjacent to said first electrode and electrically insulated from said first electrode for providing electromagnetic energy to said surface tissue;
   first electrical means coupled to said first and second electrodes for generating signals representing action potentials, and
   second electrical means coupled to said third electrode for providing said electromagnetic energy to said third electrode
   wherein said third electrode comprises a ring made of a partially conductive material of variable thickness said ring having a proximal end and a distal end, and said thickness of said ring monotonically increasing from the distal end to the proximal end of said ring.

2. The apparatus of claim 1, wherein said partially conductive material is an epoxy.

3. A method for detecting monophasic action potentials and ablating surface tissue in an in vivo heart of a patient using a catheter having a proximal end and a distal end, with a first electrode, carried at the distal end, a second electrode carried on a surface of the catheter and spaced from the first electrode, and a third electrode adjacent to but electrically insulated by a skirt member having a thickness of 0.001 to 0.200 inches from the first electrode, including the steps of:
   inserting the distal end into the heart;
   positioning the distal end in a substantially perpendicular configuration against endocardium of the heart such that the first electrode contacts said endocardium with a force sufficient to depolarize myocardial cells in the vicinity of the first electrode and such that the second electrode does not contact said endocardium;
   detecting first signals by means of said first and second electrodes, said first signals relating to the monophasic action potentials of the heart;
   at about the same time as said detecting step is performed, delivering radiofrequency energy to the heart by means of said third electrode, said energy sufficient to ablate the heart tissue; and
   repeating said detecting and delivering steps until no monophasic action potential signals are detected.

4. A method according to claim 3 wherein said detecting step and said delivering step are performed simultaneously.

5. A method for detecting monophasic action potentials and for supplying energy to ablate tissue within the heart comprising:
   introducing a catheter having a distal end in a region of the heart, the distal end of the catheter carrying first electrode means for contacting a tissue region for detecting monophasic action potentials in the contacted tissue region, indifferent second electrode means for supplying a reference potential for the first electrode means and being carried on the catheter spaced from the first electrode means, third electrode means between the first and second electrode means, the third electrode means being positioned close to the first electrode means, the third electrode means being operative for emitting energy to ablate the contacted tissue region, and means for electrically insulating the third electrode means from the first and second electrode means, bringing the first and third electrodes into contact with a tissue region within the heart, operating the first electrode means to detect monophasic action potentials in the contacted tissue region, operating the third electrode means to emit ablating energy to the contacted tissue region simultaneously with like operation of the first electrode means.

6. A method according to claim 5 wherein the steps of operating the first-and third electrode means are repeated until no monophasic action potentials are detected by the first electrode means.

7. A method for detecting monophasic action potentials and ablating tissue in the heart using a catheter having a distal end, with a first electrode carried at the distal end, a second electrode carried on a surface of the catheter and spaced from the first electrode, and a third electrode adjacent to but electrically insulated from the first electrode, including the steps of:

inserting the distal end into the heart;

positioning the distal end in a substantially perpendicular configuration against the endocardium of the heart such that the first electrode contacts the endocardium with a force sufficient to depolarize myocardial cells in the vicinity of the first electrode and such that the second electrode does not contact said endocardium;

detecting first signals by means of the first and second electrodes, said first signals relating to the monophasic action potentials of the heart;

at about the same time as the detecting step is performed, delivering ablating energy to the heart by means of the third electrode, and repeating the detecting and delivering steps until no monophasic action potential signals are detected.

8. A method according to claim 7 wherein the detecting step and the delivering step are performed simultaneously.

* * * * *